(12) United States Patent
Van Westrenen et al.

(10) Patent No.: US 8,884,090 B2
(45) Date of Patent: Nov. 11, 2014

(54) PROCESS FOR THE PREPARATION OF AN OLEFIN

(75) Inventors: Jeroen Van Westrenen, Amsterdam (NL); Leslie Andrew Chewter, Amsterdam (NL); Ferry Winter, Amsterdam (NL)

(73) Assignee: shell Oil Company, Houston, TX (US)

( * ) Notice: Subject to any disclaimer, the term of this patent is extended or adjusted under 35 U.S.C. 154(b) by 910 days.

(21) Appl. No.: 12/743,276

(22) PCT Filed: Nov. 19, 2008

(86) PCT No.: PCT/EP2008/065838
§ 371 (c)(1),
(2), (4) Date: Feb. 16, 2011

(87) PCT Pub. No.: WO01/62689
PCT Pub. Date: Aug. 30, 2001

(65) Prior Publication Data
US 2011/0160509 A1    Jun. 30, 2011

(30) Foreign Application Priority Data

Nov. 19, 2007 (EP) .................................. 07120962
Nov. 19, 2007 (EP) .................................. 07120963

(51) Int. Cl.
| | | |
|---|---|---|
| *C07C 1/20* | (2006.01) | |
| *C07C 1/24* | (2006.01) | |
| *C07C 1/00* | (2006.01) | |
| *B01J 8/04* | (2006.01) | |
| *B01J 8/26* | (2006.01) | |
| *C07C 11/02* | (2006.01) | |

(52) U.S. Cl.
CPC *B01J 8/0457* (2013.01); *B01J 8/26* (2013.01); *C07C 1/20* (2013.01); *C07C 11/02* (2013.01); *C07C 2529/40* (2013.01); *C07C 2529/85* (2013.01); *C07C 2529/89* (2013.01)
USPC ........................... 585/638; 585/639; 585/640

(58) Field of Classification Search
USPC ......................................... 585/638, 639, 640
See application file for complete search history.

(56) References Cited

U.S. PATENT DOCUMENTS 3,998,899 A  * 12/1976 Daviduk et al. ............... 585/314
4,052,479 A  * 10/1977 Chang et al. .................. 585/640

(Continued)

FOREIGN PATENT DOCUMENTS

| DE | 10027159 | 12/2001 | ................ C07C 1/20 |
| DE | 10043644 | 3/2002 | ............ C07C 29/128 |

(Continued)

OTHER PUBLICATIONS

Wetssermehl, K., et al: Industrial Organic Chemistry, 3$^{rd}$ Edition, Wiley, 1997, pp. 13-28.

(Continued)

*Primary Examiner* — In Suk Bullock
*Assistant Examiner* — Youngsul Jeong

(57) ABSTRACT

An olefin is prepared from an alkyl alcohol in a process which comprises the steps: a) converting the alkyl alcohol into a dialkylether over a first catalyst, to yield a hot dialkylether product stream containing alkyl alcohol, dialkylether and water; b) cooling the hot dialkylether product stream at least partly by indirect heat exchange with a cold dialkylether product stream to below the dew point of water at the prevailing conditions to obtain a gas-liquid mixture; c) separating the obtained mixture into a liquid water-containing stream and a vaporous dialkylether-rich stream; d) subjecting at least part of the vaporous dialkylether-rich stream, as the cold dialkylether product stream in step b), to heat exchange with the hot dialkylether product stream, to yield a heated dialkylether-rich feed; and e) converting the heated dialkylether-rich feed to an olefin over a second catalyst.

10 Claims, 2 Drawing Sheets

(56) References Cited

U.S. PATENT DOCUMENTS

| | | | |
|---|---|---|---|
| 4,076,796 A | 2/1978 | Reh et al. | 423/659 |
| 4,076,842 A | 2/1978 | Plank et al. | 423/328 |
| 4,397,827 A | 8/1983 | Chu | 423/326 |
| 4,444,988 A * | 4/1984 | Capsuto et al. | 585/415 |
| 4,556,477 A | 12/1985 | Dwyer | 208/111 |
| 4,590,320 A | 5/1986 | Sapre | 585/324 |
| 4,665,249 A | 5/1987 | Mao et al. | 585/408 |
| 5,037,511 A | 8/1991 | Dornhagen et al. | 203/37 |
| 5,367,100 A | 11/1994 | Gongwei et al. | 585/640 |
| 5,817,906 A | 10/1998 | Marker et al. | 585/640 |
| 6,046,372 A | 4/2000 | Brown et al. | 585/640 |
| 6,791,002 B1 | 9/2004 | Abrevaya et al. | 585/648 |
| 6,797,851 B2 | 9/2004 | Martens et al. | 585/640 |
| 7,232,936 B1 * | 6/2007 | Yurchak | 585/640 |
| 2003/0078463 A1 | 4/2003 | Martens et al. | 585/638 |
| 2006/0020155 A1 * | 1/2006 | Beech et al. | 585/639 |
| 2006/0135834 A1 * | 6/2006 | Xu et al. | 585/639 |
| 2007/0155999 A1 | 7/2007 | Pujado et al. | 585/327 |
| 2007/0203380 A1 | 8/2007 | Vora et al. | 585/638 |
| 2009/0105429 A1 | 4/2009 | Chewter et al. | 526/67 |
| 2009/0187058 A1 * | 7/2009 | Chewter et al. | 585/639 |

FOREIGN PATENT DOCUMENTS

| | | | |
|---|---|---|---|
| EP | 88494 | 9/1983 | C07C 1/20 |
| EP | 340576 | 11/1989 | C07C 41/00 |
| EP | 343454 | 11/1989 | C07C 41/09 |
| EP | 485145 | 5/1992 | C07C 11/02 |
| EP | 489497 | 6/1992 | C07C 11/02 |
| JP | 8074791 | 3/1996 | F04D 29/44 |
| WO | WO9522516 | 8/1995 | C07C 2/12 |
| WO | WO0162689 | 8/2001 | C07C 1/20 |
| WO | WO0185872 | 11/2001 | C10G 11/18 |
| WO | WO0192190 | 12/2001 | C07C 11/06 |
| WO | WO03020667 | 3/2003 | C07C 2/08 |
| WO | WO2004018089 | 3/2004 | B01J 8/04 |
| WO | WO2004031327 | 4/2004 | C10G 11/18 |
| WO | WO2004037950 | 5/2004 | C10G 2/00 |
| WO | WO2004056944 | 7/2004 | C10G 11/05 |
| WO | WO2006020083 | 2/2006 | C07C 1/20 |
| WO | WO2007135052 | 11/2007 | C07C 2/86 |

OTHER PUBLICATIONS

Ch. Baerlocher, et al: Database of Zeolite Structures: http://www.iza-structure.org/databases/-.

* cited by examiner

US 8,884,090 B2

PROCESS FOR THE PREPARATION OF AN OLEFIN

PRIORITY CLAIM

The present application claims priority to European Patent Application 07121005.8 filed 19 Nov. 2007; European Patent Application 07121003.3 filed 19 Nov. 2007; European Patent Application 07121014.0 filed 19 Nov. 2007; European Patent Application 07121008.2 filed 19 Nov. 2007; European Patent Application 07120962.1 filed 19 Nov. 2007 and European Patent Application 07120963.9 filed 19 Nov. 2007.

FIELD OF THE INVENTION

The present invention relates to a process for the preparation of an olefin from an alkyl alcohol. In particular it relates to a process wherein an alkyl alcohol is converted to a dialkylether and, subsequently, the reaction product is converted to an olefin, e.g. propylene or ethylene.

BACKGROUND OF THE INVENTION

Such a process is known from, e.g., WO-A 2006/020083. This document describes a process wherein methanol is converted to dimethylether in the presence of a first catalyst. Dimethylether is subsequently converted to light olefins and water in the presence of a second catalyst. In one embodiment the methanol is contacted with the first catalyst to convert methanol into dimethylether and water. Then unreacted methanol, dimethylether and water are combined with a recycle stream to form a combined stream. The combined stream is then separated into a first overhead stream comprising dimethylether and methanol and a first bottoms stream comprising a weight majority of water. The first overhead stream with dimethylether and methanol is subsequently contacted with the second catalyst to effect the conversion to light olefins and water. Finally, a portion of the water from the conversion into olefins is removed and used as the recycle stream and combined with the stream comprising dimethylether, unreacted methanol and water. Although the known process makes an attempt to integrate the dimethylether preparation and the olefin production, the process does not make effective use of the exothermic nature of the reactions.

In EP-B 88494 a process is described in which methanol is converted to dimethylether and water and, subsequently, the dimethylether is converted to olefins. The document describes that both the dimethylether preparation and the olefin production are exothermic. Therefore it is proposed to conduct the olefin production in several reaction stages, wherein use is made of interstage cooling. Moreover, it is suggested that the product from the dimethylether preparation is subjected to indirect heat exchange with, e.g., water or the methanol reactant. In the process according to EP-B 88494 water that is formed at the dimethylether preparation is only partly separated and removed after the conversion of dimethylether to olefins, together with the water produced during the conversion of dimethylether. That means that water formed at the dimethylether preparation is present at the olefin production from dimethylether and methanol. Therefore the streams through the reactions for the olefin production are unnecessarily large.

US 2006/0020155, US2007/0155999 and US2007/0203380 all disclose processes for converting synthesis gas via dimethylether to light olefins. The documents do not consider optimization of the heat integration in a process for converting an alkylalkohol stream via dialkylether to an olefinic product, in particular not starting from a relatively pure alkylalkohol stream not containing unreacted synthesis gas.

The present invention has the objective to reduce the amounts of process streams at the conversion of dimethylether to olefins, whilst improving the heat integration between the dimethylether preparation and the olefins manufacture.

SUMMARY OF THE INVENTION

Accordingly, the present invention provides a process for the preparation of an olefin from an alkyl alcohol which process comprises the steps:
a) converting the alkyl alcohol into a dialkylether over a first catalyst, to yield a hot dialkylether product stream containing alkyl alcohol, dialkylether and water;
b) cooling the hot dialkylether product stream at least partly by indirect heat exchange with a cold dialkylether product stream to below the dew point of water at the prevailing conditions to obtain a gas-liquid mixture;
c) separating the obtained gas-liquid mixture into a liquid water-containing stream and a vaporous dialkylether-rich stream;
d) subjecting at least part of the vaporous dialkylether-rich stream, as the cold dialkylether product stream in step b), to heat exchange with the hot dialkylether product stream, to yield a heated dialkylether-rich feed; and
e) converting the heated dialkylether-rich feed to an olefin over a second catalyst.

DETAILED DESCRIPTION OF THE INVENTION

Figure 1:
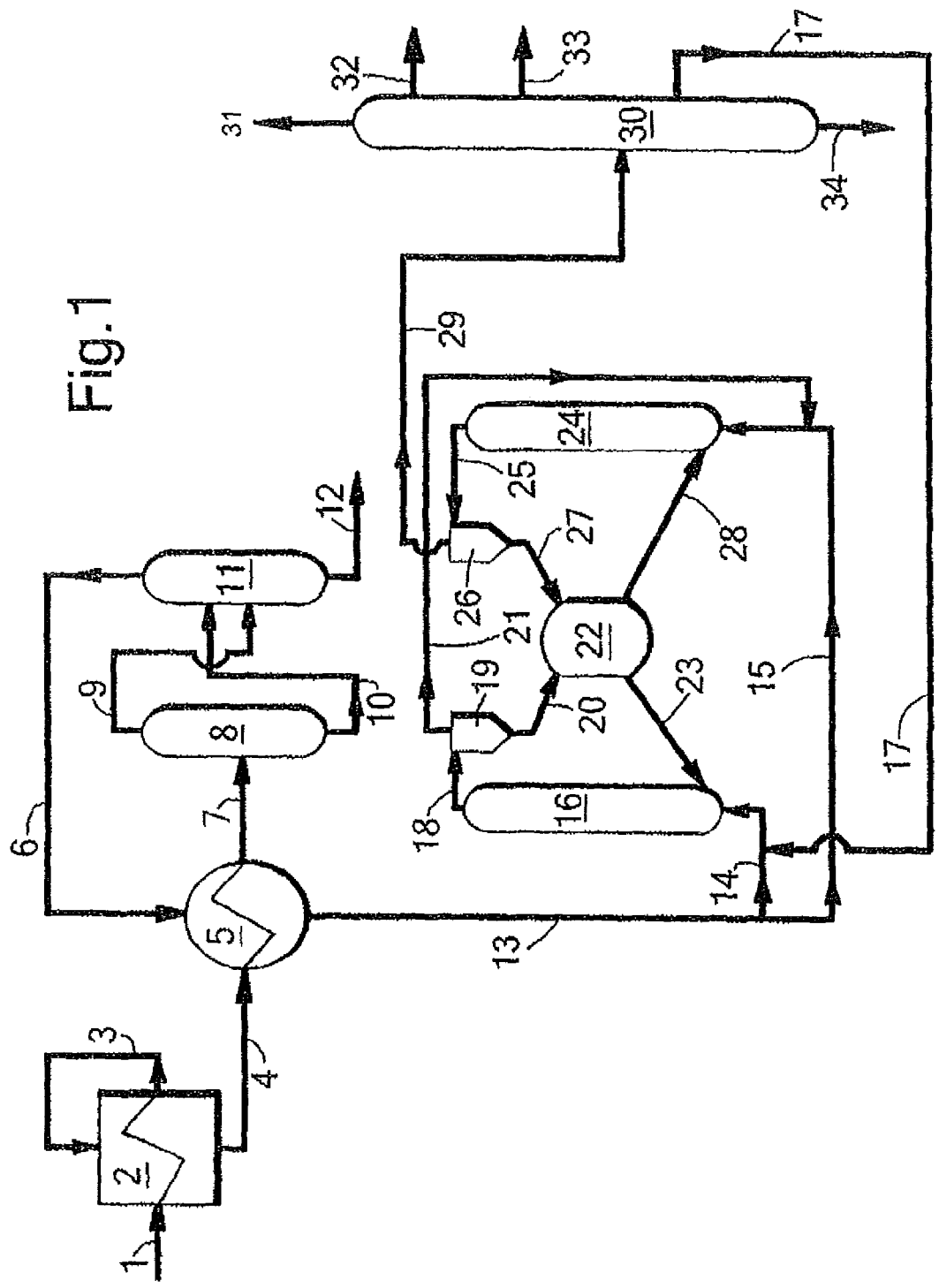
FIG. 1 is a schematic illustration of a reactor system in accordance with the invention.

In the process according to the present invention excess water formed at the alkyl alcohol conversion and present in the hot dialkylether product stream is removed from this stream so that the process streams in the olefins manufacture have reduced water content. Moreover, the remaining vaporous dialkylether-rich stream is effectively heated by using the heat of the hot dialkylether product stream.

In the process according to the present invention an alkyl alcohol is employed. Generally, the alkyl alcohol contains from 1 to 4 carbon atoms. Preferably, the alkyl alcohol is methanol. Optionally it may contain small amounts of $C_2$-$C_4$ alkyl alcohols, such as ethanol or isopropanol. The presence of such latter compounds will result in the formation of an amount of ethylmethyl ether and isopropylmethyl ether. More preferably, the alkyl alcohol is methanol with a purity of at least 99% w, preferably at least 99.5% w, based on the total weight of the reactants that are converted over the first catalyst, so that the dialkylether is substantially pure dimethylether.

In one embodiment, the vaporous alkylalkohol, in particular methanol, is obtained from an external source, i.e. the process is not integrated an upstream synthesis gas to oxygenate conversion. Therefore the vaporous alkylalkohol has typically been purified to remove unreacted synthesis gas components or does not contain synthesis gas because it was made in a different way.

The conversion of alkyl alcohol to dialkylether is known in the art. This conversion is an equilibrium reaction. In the conversion the alcohol is contacted at elevated temperature with a catalyst. In EP-A 340 576 a list of potential catalysts are described. These catalysts include the chlorides of iron, copper, tin, manganese and aluminium, and the sulphates of copper, chromium and aluminium. Also oxides of titanium, aluminium or barium can be used. Preferred catalysts include aluminium oxides and aluminium silicates. Alumina is particularly preferred as catalyst, especially gamma-alumina. Although the alkyl alcohol may be in the liquid phase the process is preferably carried out such that the alkyl alcohol is in the vapour phase. In this context the reaction is suitably carried out at a temperature of 140 to 500° C., preferably 200 to 400° C., and a pressure of 1 to 50 bar, preferably from 8-12 bar. In view of the exothermic nature of the conversion of alkyl alcohol to dialkylether the conversion of step a) is suitably carried out whilst the reaction mixture comprising the first catalyst is being cooled. It is possible to employ interstage cooling, similar to the cooling described in EP A 88494 for the conversion of methanol to olefins. Preferably, the conversion of step a) is carried out in an isothermal fashion, such that the temperature in the reaction zone is kept within a range by means of cooling. The cooling is conducted preferably with indirect heat exchange. The indirect heat exchange may take place in the reactor itself, e.g. by cooling tubes at the wall of the reactor, or by using a multitubular reactor wherein the tubes are indirectly cooled. An external heat exchanger may also be used. In such a case the process streams are at least partly circulated through the external heat exchanger and the reaction zone.

The coolant can be selected from any convenient coolants. Suitable coolants include water and/or steam. However, it is particularly useful to use the alkyl alcohol that is to be converted to the dialkylether as the coolant. This has the advantage that the reaction temperature stays within the desired limits, and at the same time the feedstock for this reaction is heated to the desired starting temperature. The coolant may be brought into indirect contact with the process streams in a counter-current, cross-current or co-current manner. It has been found that the indirect contact is preferably accomplished in a co-current manner. In this way the starting temperature of the alkyl alcohol can be kept sufficiently high so that the reaction takes place smoothly, whereas the temperature increase will be kept sufficiently low to enable a satisfactory yield of dialkylether in the equilibrium reaction.

The ratio of dialkylether and alkyl alcohol in the dialkylether product stream may vary between wide ranges. Suitable ranges include a dialkylether to alkyl alcohol weight ratio of 0.5:1 to 100:1, preferably from 2:1 to 20:1. Suitably the reaction is led to equilibrium. This includes that the dialkylether to alkyl alcohol weight ratio may vary from 2:1 to 6:1. Evidently, the skilled person may decide to influence the equilibrium by applying different reaction conditions and/or by adding or withdrawing any of the reactants.

Advantageously a pH of at least 7 is maintained in the hot dialkylether product stream, in particular in a liquid water-containing fraction of the dialkylether product stream. This stream is enriched with a base to this end. In order to enrich the dialkylether product stream with a base, the base is suitably contacted with or added to the dialkylether product stream (or a fraction thereof), such that a pH of from 7 to 12 is achieved in a liquid water-containing fraction of the dialkylether product stream. Such a base can be sodium or potassium hydroxide, or any other alkali metal or alkaline earth metal bases or mixtures thereof. The base may be added to the hot dialkylether product stream or in any preceding stream.

In the process of the present invention the hot dialkylether product stream conveniently has a temperature of 200 to 400° C. The heat of this product stream can suitably be used to increase the temperature of the dialkylether that is to be used in the subsequent olefins manufacture. Therefore, in step b) of the process of this invention the hot dialkylether product stream is subjected to indirect heat exchange with a cold dialkylether product stream. At the heat exchange the cold dialkylether product stream is heated up to become the dialkylether-rich feed for the olefins manufacture. This step b) may be carried out in one or more steps. It is advantageous to carry out the cooling in at least two steps. In the first step the hot dialkylether product stream is suitably subjected to heat exchange with the cold dialkylether product stream to yield a heat-exchanged product stream. Suitably the temperature of the heat-exchanged product stream has been lowered by 50 to 150° C. That may mean that the heat exchanged product stream has a temperature in the range of 150 to 350° C. Such values advantageously keep the heat-exchanged product stream in the gaseous phase which makes further processing relatively easy and enables a sufficiently high temperature of the dialkylether-rich feed for the olefins manufacture. In one or more subsequent steps the heat-exchanged product stream is cooled further to a temperature below the dew point of water at the prevailing conditions. Advantageously, the heat-exchanged product is cooled further by indirect heat exchange and/or by flashing. Flashing is particularly preferred since that allows not only the reduction in temperature but also a simultaneous separation of the mixture into a liquid water-containing stream and a vaporous dialkylether-rich stream. Moreover, it allows, in cases where the dialkylether production is carried out at higher pressures, for the pressure to be reduced to the desired pressure for the conversion of dialkylether to olefins. The temperature of the gas-liquid mixture, obtained in either one or more cooling steps, has suitably a value of 75 to 150° C.

Irrespective of the separation that has been achieved in the flashing step, the gas-liquid mixture obtained may be separated in a fractionation column. This allows for a more strict separation between water and dialkylether and unconverted alkyl alcohol that may be present in the respective process streams. Since the alkyl alcohol is a valuable product and since it may react in the olefins manufacture step, the separation of the gas-liquid mixture yields a liquid water-containing stream and a vaporous dialkylether-rich stream, wherein the majority of the alkyl alcohol is contained in the vaporous dialkylether-rich stream. It is within the skill of the artisan to determine the correct conditions in a fractionation column to arrive at such a separation. He may choose the correct conditions based on, i.a., fractionation temperature, pressure, trays, reflux and reboiler ratios. The conditions are preferably chosen such that the liquid-water stream contains up to 1% wt of alkyl alcohol, based on the total of water and alkyl alcohol. Since water is normally produced in the olefins manufacture step it is not required to remove all water from the dialkylether-rich stream. The dialkylether-rich stream suitably contains at most 5% wt, preferably at most 1% wt of water, based on the total weight of water, alkyl alcohol and dialkylether. The gas-liquid mixture is preferably separated into the vaporous dialkylether-rich stream having a temperature of 75 to 140° C., and the liquid water-containing stream having a temperature of 80 to 175° C. The liquid-water stream can be discharged. At least a portion of the vaporous dialkylether-rich stream, as the cold dialkylether product stream in step b), is subjected to indirect heat exchange with hot dialkylether product from step a) so that this portion is heated up and can be used as dialkylether rich feed in the olefins manufacture. Preferably, the entire vaporous dialkylether-rich stream is subjected to heat exchange.

It is preferred that the dialkylether-rich feed is heated up to a temperature ranging from 200 to 370° C., suitably from 200 to 350° C. This will provide an adequate starting temperature for the olefins conversion in step e) of the process according to the present invention, and moreover, will absorb sufficient heat from the hot dialkylether product to obtain an effective energy balance.

The olefins manufacture from dialkylether is known in the art. For instance, in the above-mentioned WO-A 2006/020083 the manufacture of olefins from dimethylether has been described. The catalysts described therein are also suitable for the process of the present invention. Such catalysts preferably include molecular sieve catalyst compositions. Excellent molecular sieves are silicoaluminophosphates (SAPO), such as SAPO-17, -18, -34, -35, -44, but also SAPO-5, -8, -11, -20, -31, -36, -37, -40, -41, -42, -47 and -56. Alternatively, the olefin manufacture may be accomplished by the use of an aluminosilicate catalyst. Suitable catalysts include those containing a zeolite of the MFI type, such as ZSM-5, the MTT type, such as ZSM-23, the TON group, such as ZSM-22, the STF-type, such as SSZ-35, the SFF type, such as SSZ-44 and the EU-2 type, such as ZSM-48. Preferably, the dialkylether-rich feed is converted over a catalyst comprising a zeolite that has one-dimensional 10-ring channels. Such a zeolite is more preferably selected from the group consisting of aluminosilicates of the MTT and TON type and mixtures thereof. The present invention is of particular advantage for processes wherein the olefin conversion is accomplished over a catalyst comprising a zeolite having one-dimensional 10-ring channels, in particular of the MTT and/or TON type, since it has been found that the hydrothermal deactivation of the catalyst is reduced when the dialkylether-rich feed stream contains no or only minor amounts, i.e. <5% wt, of water. Advantageously, the catalyst comprises one or more zeolites, of which at least 50% wt has one-dimensional 10-ring channels, such as zeolites of the MTT and/or TON type. In a particularly preferred embodiment the catalyst comprises in addition to one or more zeolites having one-dimensional 10-ring channels, such as of the MTT and/or TON type, a zeolite with more-dimensional channels in particular of the MFI type, more in particular ZSM-5, since this additional zeolite has a beneficial effect on the stability of the catalyst in the course of the process and under hydrothermal conditions.

Especially when the olefins manufacture is carried out over a catalyst containing MTT or TON type aluminosilicates, it may be advantageous to add an olefin-containing co-feed together with the dialkylether-rich feed to the reaction zone when the latter feed is introduced into this zone. It has been found that the catalytic conversion of dialkylether to olefins is enhanced when an olefin is present in the contact between dialkylether and catalyst. Therefore, suitably, an olefinic co-feed is added to the reaction zone together with the dialkylether-rich feed when one reaction zone is employed. When multiple reaction zones are employed, an olefinic co-feed is advantageously added to the part of the dialkylether-rich feed that is passed to the first reaction zone.

The olefinic co-feed may contain one olefin or a mixture of olefins. Apart from olefins, the olefinic co-feed may contain other hydrocarbon compounds, such as for example paraffinic, alkylaromatic, aromatic compounds or a mixture thereof. Preferably the olefinic co-feed comprises an olefinic fraction of more than 50 wt %, more preferably more than 60 wt %, still more preferably more than 70 wt %, which olefinic fraction consists of olefin(s). The olefinic co-feed can consist essentially of olefin(s).

Any non-olefinic compounds in the olefinic co-feed are preferably paraffinic compounds. If the olefinic co-feed contains any non-olefinic hydrocarbon, these are preferably paraffinic compounds. Such paraffinic compounds are preferably present in an amount in the range from 0 to 50 wt %, more preferably in the range from 0 to 40 wt %, still more preferably in the range from 0 to 30 wt %.

By an olefin is understood an organic compound containing at least two carbon atoms connected by a double bond. A wide range of olefins can be used. The olefin can be a mono-olefin, having one double bond, or a poly-olefin, having two or more double bonds. Preferably olefins present in the olefinic co-feed are mono-olefins.

The olefin(s) can be a linear, branched or cyclic olefin. Preferably olefins present in the olefinic co-feed are linear or branched olefins.

Preferred olefins have in the range from 2 to 12, preferably in the range from 3 to 10, and more preferably in the range from 4 to 8 carbon atoms.

Examples of suitable olefins that may be contained in the olefinic co-feed include ethene, propene, butene (one or more of 1-butene, 2-butene, and/or iso-butene (2-methyl-1-propene)), pentene (one or more of 1-pentene, 2-pentene, 2-methyl-1-butene, 2-methyl-2-butene, 3-methyl-1-butene, and/or cyclopentene), hexene (one or more of 1-hexene, 2-hexene, 3-hexene, 2-methyl-1-pentene, 2-methyl-2-pentene, 3-methyl-1-pentene, 3-methyl-2-pentene, 4-methyl-1-pentene, 4-methyl-2-pentene, 2,3-dimethyl-1-butene, 2,3-dimethyl-2-butene, 3,3-dimethyl-1-butene, methylcyclopentene and/or cyclohexene), heptenes, octenes, nonenes and decenes. The preference for specific olefins in the olefinic co-feed may depend on the purpose of the process.

In a preferred embodiment the olefinic co-feed preferably contains olefins having 4 or more carbon atoms (i.e. $C_{4+}$ olefins), such as butenes, pentenes, hexenes and heptenes. More preferably the olefinic fraction of the olefinic co-feed comprises at least 50 wt % of butenes and/or pentenes, even more preferably at least 50% wt of butenes, and most preferably at least 90 wt % of butenes. The butene may be 1-, 2-, or iso-butene. Most conveniently it is a mixture thereof. More preferably, the olefinic co-feed that is added to the reaction zone is a by-product of the olefin conversion step e) of the present process which by-product contains 4 or more, such as 4 to 7, preferably just 4, carbon atoms and which is recycled to the reaction zone. These relatively higher olefins tend to facilitate the conversion of dialkylether to olefins such as propylene and ethylene. If a particularly high yield of ethylene is desired, part or all of C3 components from the effluent of the olefin conversion step e), in particular part or all of propene, can be recycled as part of the olefinic co-feed.

The reaction conditions of the olefin manufacture include those that are mentioned in WO-A 2006/020083. Hence, a reaction temperature of 200 to 1000° C., preferably from 250 to 750° C., and a pressure from 0.1 kPa (1 mbar) to 5 MPa (50 bar), preferably from 100 kPa (1 bar) to 1.5 MPa (15 bar), are suitable reaction conditions.

The reaction of the dialkylether-rich feed may be carried out in a single reaction zone, as described in WO-A 2006/020083. However, it is preferred that the conversion takes place in several reaction zones into each of which heated dialkylether-rich feed is fed. Accordingly, part of the heated dialkylether-rich feed is passed to multiple reaction zones comprising a first reaction zone and one or more subsequent reaction zones, where the heated dialkylether-rich feed is converted to an olefin. Evidently, the multiple reaction zones may be operated in parallel. However, it is preferred that the multiple reaction zones are arranged in series. In that way at least part or substantially all of the product of the previous reaction zone is forwarded to the subsequent reaction zone. Also the catalyst of the previous reaction zone may be forwarded to the subsequent reaction zone together with its product, i.e. the entire effluent from a previous reaction zone can be forwarded. Hence, the number of reaction zones may suitably vary from 1 to 6, preferably from 2 to 4.

It is advantageous to ensure that the temperature of the heated dialkylether-rich feed that is passed to the only reaction zone or the temperature of the part of the heated dialkylether-rich feed that is passed to the first of multiple reaction zones has a temperature of 300 to 700° C. This allows that, after mixing with the catalyst and, optionally, with an olefinic co-feed, a reactor inlet temperature is provided at which the conversion quickly starts. To obtain this desired temperature it may be convenient to heat the dialkylether-rich feed that comes from step d) further. Since the conversion of dialkylether to olefins is exothermic the reaction temperature tends to increase. Further heating may be accomplished by use of an external heater or by mixing the feed with hot catalyst particles, e.g., when these particles are obtained from their regeneration. Since under these conditions also alkyl alcohol can be converted into olefins, it is beneficial to ensure that most, if not all, of unreacted alkyl alcohol from step a) of the current process is included in the dialkylether-rich feed.

As indicated above, it is preferred that the reaction is carried out in multiple reaction zones in series, into each of which zones dialkylether is fed as starting material. For the subsequent reaction zones, the dialkylether-rich feed does not need to have the same high temperature as the part that is fed to the first reaction zone. In these cases it suitably has a temperature of 50 to 350° C. The desired additional heat may be provided by the catalyst and/or product of the preceding reaction zone that has been heated by the exothermic reaction in this preceding reaction zone. The desired temperature may also be provided by any additional catalyst that is fed from a catalyst regeneration zone to such subsequent reaction zone. Moreover, there is no need to pass additional olefins into the subsequent reaction zones. Since a lower temperature may suffice for the heated dialkylether-rich feed the feed that comes straight from step d) may be used in any subsequent reaction zone without further heating steps and without addition of optional olefins. Alternatively, the dialkylether-rich feed may be cooled before being fed to a subsequent reaction zone.

The reaction zone or zones may be comprised in a variety of reactors. Suitable reactors include fixed bed reactors, fluidised bed reactor, circulating fluidised bed reactors, riser reactors, and the like. Suitable reactor types have been described in U.S. Pat. No. 4,076,796. Preferred reactors are riser reactors. Hence, the conversion of dialkylether to olefins is preferably carried out in multiple reaction zones wherein the multiple reaction zones have been executed as multiple riser reactors.

Figure 2:
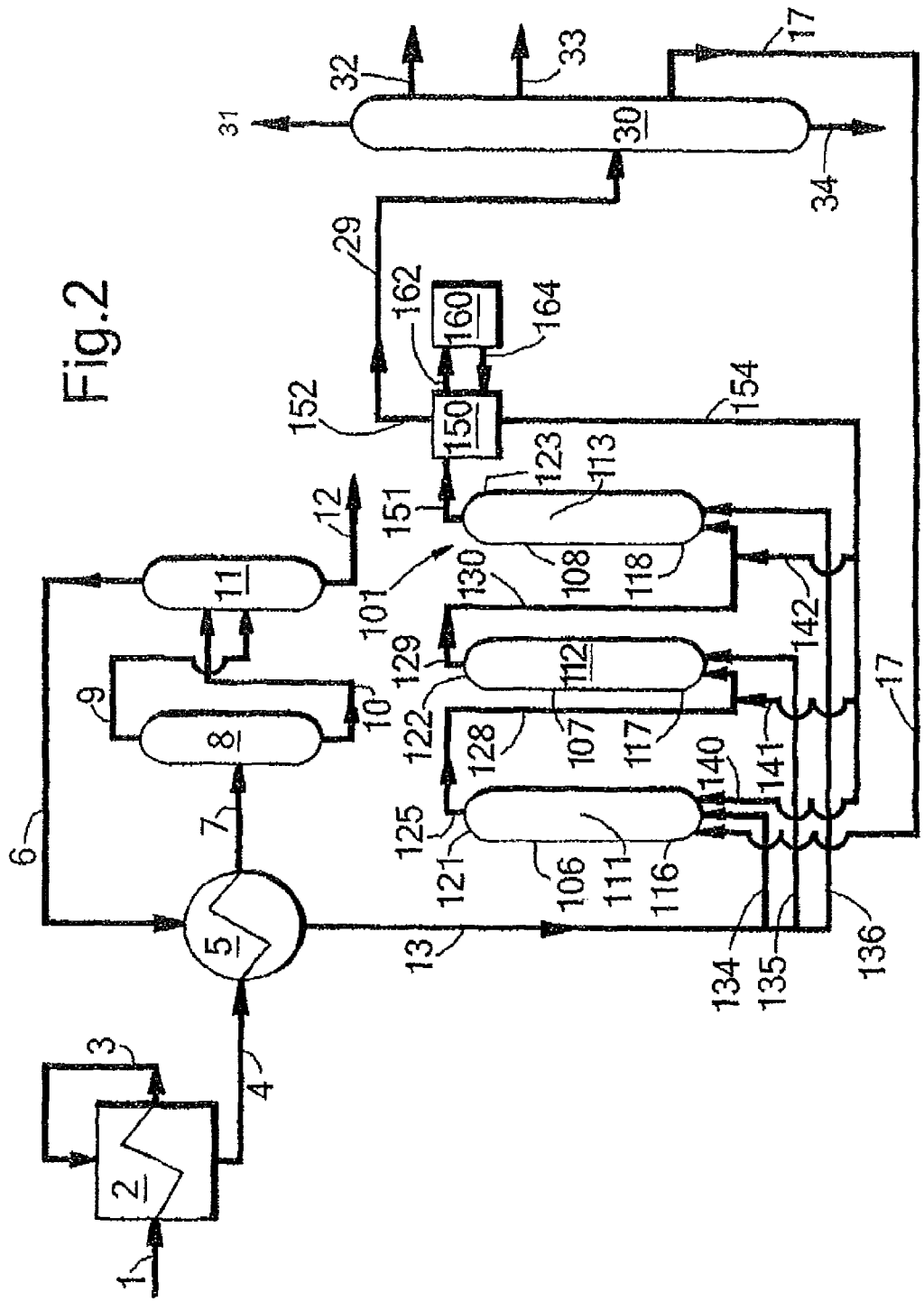
FIG. 2 is a schematic illustration of another embodiment of the invention.

The process of the present invention will be elucidated by reference to the accompanying FIGS. 1 and 2.

In FIG. 1 vaporous alkyl alcohol is passed via a line 1 through coolant tubes in a dialkylether reactor 2. The vaporous alkylalkohol in this embodiment can be obtained from an external source, and does not contain unreacted synthesis gas. As the formation of dialkylether from alkyl alcohol is exothermic, the vaporous alkyl alcohol is heated and the thus heated alkyl alcohol leaves the reactor as hot effluent via a line 3. The hot effluent is subsequently recycled to the reactor 2 but at the reaction side of the coolant tubes. The stream from line 1 and the one from line 3 are passed co-currently through reactor 2. In reactor 2 the alkyl alcohol is converted to dialkylether and water in contact with a suitable catalyst, e.g. gamma-alumina. A dialkylether product stream comprising dialkylether, water and alkyl alcohol leaves the reactor via a line 4. The hot dialkylether product stream is cooled in two stages. In the first stage the hot product stream in the line 4 is subjected to indirect heat exchange in heat exchanger 5, wherein it is brought in indirect contact with a cold dialkylether product stream fed via a line 6. A heat-exchanged product stream comprising dialkylether, alkyl alcohol and water, but preferably still in the vaporous phase leaves the heat exchanger 5 via a line 7 and is passed to a flash vessel 8. In the flash vessel 8 the pressure is reduced and the product stream is cooled further to below the dew point of water. The vaporous effluent from the flash vessel 8 comprises most of the dialkylether and some alkyl alcohol and leaves the flash vessel via a line 9. The liquid effluent, comprising water and alkyl alcohol, leaves the flash vessel 8 via a line 10. The effluents from lines 9 and 10 are both fed into a fractionation column 11, whereby line 10 debouches into the fractionation column 11 at a point above the location where line 9 debouches into column 11. In fractionation column 11 the gas-liquid mixture, obtained from both streams, is separated into a liquid stream 12 comprising water and less than 1% wt alkyl alcohol, based on the total of water and alkyl alcohol, and a vaporous dialkylether-rich stream 6, comprising dialkylether, the majority of the alkyl alcohol and typically some water. The vaporous dialkylether-rich stream is used as the cold dialkylether product stream in heat exchanger 5.

In heat exchanger 5 the cold dialkylether product stream is heated up to become a heated dialkylether-rich feed that leaves the heat exchanger 5 via line 13. The stream in line 13 may be split into several portions. In the case of the present figure there are two portions, but it will be evident that when more portions are desired in view of the number of reactors the number can be adapted. The portion in line 14 is fed to a first riser reactor 16 of a serial riser reactor system, whereas the portion in line 15 is fed to a second riser reactor 24 of the serial riser reactor system. The stream in line 14 may be further heated (not shown), e.g. by additional heat exchange or other heating means. The stream is combined with a stream of an olefinic co-feed, comprising olefins with 4 and/or 5 carbon atoms which stream is provided via a line 17.

In the riser reactor 16 the streams from lines 14 and 17 are contacted with a suitable catalyst, provided via a line 23, and the formed combination of oxygenate (i.e. dialkylether and alkyl alcohol), olefin, water and catalyst is passed upwards and this combination leaves the riser reactor 16 via a line 18 as reaction product.

The lines 14 and 17 are shown as combined before entering the riser reactor 16, but it will be understood that each may debouch into riser reactor 16 separately. Alternatively, line 23 is shown as a separate line, but it will be understood that it may be combined with any of the two other lines 14 and 17 before entering the riser reactor 16.

Via line 18 the reaction product is passed to a separation means, e.g. a cyclone 19, from which catalyst particles are discharged via a line 20 and passed to a catalyst buffer vessel 22, and from which the vaporous reaction product, comprising dialkylether, olefins and water is withdrawn via line 21. This vaporous product in line 21 is combined with the portion of the dialkylether-rich feed in line 15 and passed to the second riser reactor 24, in which a similar reaction takes place as in riser reactor 16. Catalyst for riser reactor 24 is provided via line 28. The reaction product of the riser reactor 24 is discharged therefrom via line 25 and passed to a separation means 26, e.g. a cyclone. In the separation means catalyst particles are separated from the vaporous products and withdrawn from the separation means 26 via a line 27 and passed to the catalyst buffer vessel 22.

In another embodiment the reaction product in line 18 is passed to reactor 24 in its entirety and separation of all catalysts and vaporous product will take place in cyclone 26. From cyclone 26 the catalysts are passed to collection vessel 22 and catalyst will be passed to the reactors 16 and 24 via the lines 23 and 28, respectively.

It will be realised that at the dialkylether conversion reaction some coke formation may take place, which coke may deposit on the catalyst particles. Therefore, it is advantageous to regenerate the catalyst particles periodically. Conveniently this may be achieved by continuously or periodically withdrawing part of the catalyst inventory of the catalyst buffer vessel 22 and passing it to a regeneration vessel (not shown), where typically coke is burned partially or substantially fully at temperatures of about 600° C. or more. The size of the portion sent to the regeneration vessel depends on the average degree of deactivation or coking, and on the regeneration conditions, e.g. partial or full burning of coke. The regenerated catalyst particles are recycled to the catalyst buffer vessel or to the riser reactor(s) directly. The regeneration is not shown in the figure.

As product from the separation means 26 an olefins-containing product stream is obtained in a line 29. This product is passed to a fractionation section, in the figure represented by a column 30 in which the olefins-containing product stream is separated into a light fraction 31, comprising light contaminants, such as carbon monoxide, carbon dioxide and methane, into an ethylene fraction 32, into a propylene fraction 33 and into a $C_4$ olefin fraction 17. Optionally, one or more heavier fractions, e.g. fractions with hydrocarbons with 5, 6 or 7+ hydrocarbons may be withdrawn separately from the column 30 (not shown). The separation section also includes a line 34 for withdrawing water. The light fraction in line 31 is discharged, e.g., combusted as fuel. Ethylene and propylene are recovered as products. Water in fraction 34 is withdrawn, and the $C_4$ fraction is recycled via line 17 to the dialkylether-rich feed in line 14.

The figure shows two riser reactors. It will be evident to the skilled person that only one reactor or more than two, e.g., 3 or 4, riser reactors may be used. Such use will also get the benefits of the present invention.

A further embodiment is schematically shown in FIG. 2. Like reference numerals as in FIG. 1 are used to refer to the same or similar objects. The difference between the embodiments of FIGS. 1 and 2 is in the serial riser reactor system used for step d) of the method of the invention, and it suffices to discuss this difference.

The serial reactor system 101 has three riser reactor zones 106, 107, 108 each having a single riser reactor 111, 112, 113, which riser reactors are serially arranged. Zone 106 with riser 111 is the first riser reactor zone, zone 107 with riser 112 is the second, and zone 108 with riser 113 is the third. Each riser has at its lower end an inlet end 116, 117, 118 with one or more inlets, and at its upper end an outlet end 121, 122, 123 with one or more outlets. The outlet 125 of the first riser 111 is connected via a conduit 128, such as a downer, to the inlet end 117 of the second riser 112. Likewise, outlet 129 of the second riser 112 is connected via a conduit 130 to the inlet end 118 of the third riser 113.

Each riser is moreover arranged to receive oxygenate at its inlet end, via conduits 134, 135, 136 which are all connected to the heated dialkylether-rich feed line 13. The first riser 111 has moreover an inlet for an olefinic co-feed from line 17, and an inlet for catalyst via line 140. The feed lines 134, 17 and 140 are shown to enter the inlet end 116 separately, but it will be understood that any two or all three feed lines can be combined before entering the inlet end 116.

To the effluent from riser 111, entering the inlet end 117 of the second riser 112 is added further catalyst via line 141, wherein it will be understood that the catalyst can alternatively be added to the inlet end 117 directly. Likewise, catalyst is added to the inlet end 118 of riser 113 via line 142.

The outlet from the last riser 113 is connected to a collector and separation means 150 via line 151. The separation means 150 can also be integrated with the outlet end of the last riser. It can be a large collector vessel combined with a plurality of cyclone separators, which can be internally housed in the collector vessel. The means 150 has an outlet for vapour 152 and an outlet for catalyst 154, to which catalyst feed lines 140, 141, 142 are connected. There is moreover provided a catalyst regeneration unit 160 which is arranged to receive catalyst via line 162 and returns regenerated catalyst to the means 150 via line 164.

During normal operation of the serial reactor system 101, the heated dialkylether-rich feed from line 13, olefinic co-feed and catalyst are fed via lines 134, 17, 140, respectively, to the inlet end 116 of the first riser 111. Conversion in the first riser 111 over the catalyst forms an olefinic first reactor effluent comprising a gaseous product comprising olefins, and catalyst. Substantially the entire reactor effluent is fed in this embodiment via line 128 to the inlet end 117 of the second riser 112, together with oxygenate from line 135 and additional catalyst via line 141. Although it is possible to also feed an olefinic co-feed to the second riser 112, this is not needed and not necessarily advantageous, since the effluent from reactor 111 already contains olefins.

Additional catalyst is added via line 141. Thus, the mass flow rate (mass per unit of time) of oxygenate conversion catalyst in the second riser is higher than in the first riser reactor. As shown in the drawing, it is premixed with the reactor effluent in line 129, but can also directly be admitted to the inlet end 117. The cross-section of the second riser is larger than that of the first riser. A useful design rule is to choose the cross-section increase from one riser to the next such that the weight hourly space velocity remains substantially constant, i.e. not deviating more than 50% from that of the previous riser reactor. For cylindrical risers, the increase in cross-section can also be expressed as an increase in diameter.

When the weight hourly space velocity is substantially constant, the time to flow through the riser is the same for risers of the same height.

The conversion in the second riser 112 proceeds similar to that in the first riser 111, wherein the role of the olefinic co-feed is taken over by the olefinic product in the effluent from the first riser.

Effluent from the second riser 112 is fed to the inlet end 118 of the third riser 113, and combined with additional feeds of oxygenate via line 136 and oxygenation catalyst via line 142, in principle in the same way as discussed for the inlet end 117 of the second riser 112.

The cross section of the third riser 113 is again larger than that of the second riser. It can be preferred to design each riser and the respective catalyst throughput such that substantially full conversion of oxygenate is achieved in the riser, this can be most desirable for the last riser so that substantially no oxygenate forms part of the effluent from the last riser.

The effluent from the outlet end 123 of the last riser 113 comprises olefin-containing product and catalyst. The olefin-containing product is separated from the catalyst in the collection and separation means 150.

Under typical operating conditions the deactivation of catalyst, such as due to coking, occurs on a timescale much longer than the average contact time the riser reactors. In such circumstances it is not needed to regenerate all of the catalyst from line 151 simultaneously. It is rather sufficient then to only send a portion of the catalyst to the catalyst regeneration unit 160, where typically coke is burned partially or substantially fully at temperatures of about 600° C. or more. The size of the portion sent to the regeneration unit 160 depends on the average degree of deactivation or coking, and on the regeneration conditions, e.g. partial or full burning of coke.

The olefins-containing product stream in line 29 is sent to the fractionation section, column 30, and partially recycled as discussed with reference to FIG. 1.

What is claimed is:

1. A process for the preparation of an olefin from an alkyl alcohol which process comprises:
   a) converting the alkyl alcohol into a dialkylether over a first catalyst, to yield a hot dialkylether product stream containing alkyl alcohol, dialkylether and water;
   b) cooling the hot dialkylether product stream at least partly by indirect heat exchange with a cold dialkylether product stream to below the dew point of water at the prevailing conditions to obtain a gas-liquid mixture;
   c) separating the obtained gas-liquid mixture into a liquid water-containing stream and a vaporous dialkylether-rich stream;
   d) subjecting at least part of the vaporous dialkylether-rich stream, as the cold dialkylether product stream in step b), to indirect heat exchange with the hot dialkylether product stream, to yield a heated dialkylether-rich feed; and
   e) converting the heated dialkylether-rich feed to an olefin over a second catalyst.

2. The process as claimed in claim 1, wherein the alkyl alcohol is methanol.

3. The process as claimed in claim 1, wherein step a) is carried out whilst the reaction mixture comprising the first catalyst is being cooled.

4. The process as claimed in claim 1, wherein the cooling in step b) is carried out in at least two steps.

5. The process as claimed in claim 4, wherein in a first step the hot dialkylether product stream is subjected to heat exchange with the cold dialkylether product stream to yield a heat-exchanged product stream, and the heat-exchanged product stream is cooled further by indirect heat exchange and/or by flashing.

6. The process as claimed in claim 1, wherein the conversion of dialkylether takes place in multiple reaction zones into each of which the heated dialkylether-rich feed is fed.

7. The process as claimed in claim 1, wherein the second catalyst includes molecular sieve catalyst compositions.

8. The process as claimed in claim 7, wherein the dialkylether-rich stream is converted over a catalyst comprising a zeolite selected from the group consisting of aluminosilicates having one-dimensional 10-ring channels.

9. The process as claimed in claim 1, wherein an olefinic co-feed is added to the heated dialkylether-rich feed.

10. The process as claimed in claim 9, wherein the olefinic co-feed comprises at least 50% wt of butenes, based on the total weight of the olefinic co-feed.

* * * * *